US012805902B2

(12) United States Patent
Mast

(10) Patent No.: US 12,805,902 B2
(45) Date of Patent: Nov. 24, 2026

(54) SYSTEM AND METHOD FOR PORT PLACEMENT IN A SURGICAL ROBOTIC SYSTEM

(71) Applicant: Covidien LP, Mansfield, MA (US)

(72) Inventor: Nathaniel C. Mast, Hamden, CT (US)

(73) Assignee: Covidien LP, Mansfield, MA (US)

( * ) Notice: Subject to any disclaimer, the term of this patent is extended or adjusted under 35 U.S.C. 154(b) by 286 days.

(21) Appl. No.: 18/228,900

(22) Filed: Aug. 1, 2023

(65) Prior Publication Data

US 2024/0058031 A1 Feb. 22, 2024

Related U.S. Application Data

(60) Provisional application No. 63/398,246, filed on Aug. 16, 2022.

(51) Int. Cl.

| | |
|---|---|
| ***A61B 17/34*** | (2006.01) |
| ***A61B 34/30*** | (2016.01) |
| ***A61B 90/00*** | (2016.01) |
| *A61B 17/00* | (2006.01) |
| *A61B 34/10* | (2016.01) |

(52) U.S. Cl.

CPC ...... *A61B 17/3403* (2013.01); *A61B 17/3423* (2013.01); *A61B 34/30* (2016.02); *A61B 90/361* (2016.02); *A61B 2017/00907* (2013.01); *A61B 2017/00951* (2013.01); *A61B 2034/107* (2016.02); *A61B 2034/302* (2016.02); *A61B 2090/366* (2016.02); *A61B 2090/395* (2016.02)

(58) Field of Classification Search

CPC ...... A61B 2090/366; A61B 2090/3937; A61B 2090/395; A61B 17/3423; A61B 17/3403; A61B 17/34

See application file for complete search history.

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |

(Continued)

*Primary Examiner* — Scott Luan

(74) *Attorney, Agent, or Firm* — Carter, DeLuca & Farrell LLP

(57) ABSTRACT

A surgical robotic system includes a robotic arm, a computer, and a printing device. The robotic arm includes a surgical instrument and the computer is configured to calculate port placement locations based on an image of a patient and a type of procedure to be performed. The printing device is configured to print a template of the port placement locations on a transparent substrate for placement on the patient based on the port placement locations calculated by the computer.

20 Claims, 7 Drawing Sheets

(56) References Cited

U.S. PATENT DOCUMENTS 6,676,684 B1 1/2004 Morley et al.
6,685,698 B2 2/2004 Morley et al.
6,699,235 B2 3/2004 Wallace et al.
6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.
8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.
8,912,746 B2 12/2014 Reid et al.
8,944,070 B2 2/2015 Guthart
8,989,903 B2 3/2015 Weir et al.
9,002,518 B2 4/2015 Manzo
9,014,856 B2 4/2015 Manzo et al.

(56) References Cited

U.S. PATENT DOCUMENTS

| | | | |
|---|---|---|---|
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,111,716 | B2 | 10/2018 | Carol |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |

(56) References Cited

U.S. PATENT DOCUMENTS

| | | | | |
|---|---|---|---|---|
| 11,076,925 | B2 | 8/2021 | DiMaio et al. | |
| 11,090,119 | B2 | 8/2021 | Burbank | |
| 11,096,687 | B2 | 8/2021 | Flanagan et al. | |
| 11,098,803 | B2 | 8/2021 | Duque et al. | |
| 11,109,925 | B2 | 9/2021 | Cooper et al. | |
| 11,116,578 | B2 | 9/2021 | Hoffman et al. | |
| 11,129,683 | B2 | 9/2021 | Steger et al. | |
| 11,135,029 | B2 | 10/2021 | Suresh et al. | |
| 11,147,552 | B2 | 10/2021 | Burbank et al. | |
| 11,147,640 | B2 | 10/2021 | Jarc et al. | |
| 11,154,373 | B2 | 10/2021 | Abbott et al. | |
| 11,154,374 | B2 | 10/2021 | Hanuschik et al. | |
| 11,160,622 | B2 | 11/2021 | Goldberg et al. | |
| 11,160,625 | B2 | 11/2021 | Wixey et al. | |
| 11,161,243 | B2 | 11/2021 | Rabindran et al. | |
| 11,166,758 | B2 | 11/2021 | Mohr et al. | |
| 11,166,770 | B2 | 11/2021 | DiMaio et al. | |
| 11,166,773 | B2 | 11/2021 | Ragosta et al. | |
| 11,173,597 | B2 | 11/2021 | Rabindran et al. | |
| 11,185,378 | B2 | 11/2021 | Weir et al. | |
| 11,191,596 | B2 | 12/2021 | Thompson et al. | |
| 11,197,729 | B2 | 12/2021 | Thompson et al. | |
| 11,213,360 | B2 | 1/2022 | Hourtash et al. | |
| 11,221,863 | B2 | 1/2022 | Azizian et al. | |
| 11,234,700 | B2 | 2/2022 | Ragosta et al. | |
| 11,241,274 | B2 | 2/2022 | Vaders et al. | |
| 11,241,290 | B2 | 2/2022 | Waterbury et al. | |
| 11,259,870 | B2 | 3/2022 | DiMaio et al. | |
| 11,259,884 | B2 | 3/2022 | Burbank | |
| 11,272,993 | B2 | 3/2022 | Gomez et al. | |
| 11,272,994 | B2 | 3/2022 | Saraliev et al. | |
| 11,291,442 | B2 | 4/2022 | Wixey et al. | |
| 11,291,513 | B2 | 4/2022 | Manzo et al. | |
| 11,376,002 | B2 | 7/2022 | Shelton, IV et al. | |
| 11,376,098 | B2 | 7/2022 | Shelton, IV et al. | |
| 11,381,759 | B2 | 7/2022 | Zhao et al. | |
| 11,382,621 | B2 | 7/2022 | Scheib et al. | |
| 11,382,624 | B2 | 7/2022 | Harris et al. | |
| 11,382,625 | B2 | 7/2022 | Huitema et al. | |
| 11,382,626 | B2 | 7/2022 | Shelton, IV et al. | |
| 11,382,627 | B2 | 7/2022 | Huitema et al. | |
| 11,382,638 | B2 | 7/2022 | Harris et al. | |
| 11,382,644 | B2 | 7/2022 | Schoettgen et al. | |
| 11,389,160 | B2 | 7/2022 | Shelton, IV et al. | |
| 11,389,255 | B2 | 7/2022 | DiMaio et al. | |
| 11,399,906 | B2 | 8/2022 | Shelton, IV et al. | |
| 11,406,379 | B2 | 8/2022 | Hess et al. | |
| 11,410,259 | B2 | 8/2022 | Harris et al. | |
| 11,419,630 | B2 | 8/2022 | Yates et al. | |
| 11,424,027 | B2 | 8/2022 | Shelton, IV | |
| 11,432,888 | B2 | 9/2022 | Diolaiti et al. | |
| 11,432,893 | B2 | 9/2022 | Itkowitz et al. | |
| 11,432,895 | B2 | 9/2022 | Loh et al. | |
| 11,439,390 | B2 | 9/2022 | Patel et al. | |
| 11,439,391 | B2 | 9/2022 | Bruns et al. | |
| 11,468,791 | B2 | 10/2022 | Jarc et al. | |
| 11,471,155 | B2 | 10/2022 | Shelton, IV et al. | |
| 11,471,221 | B2 | 10/2022 | Zhao et al. | |
| 11,478,308 | B2 | 10/2022 | Hoffman et al. | |
| 11,490,977 | B2 | 11/2022 | Schena et al. | |
| 11,497,499 | B2 | 11/2022 | Shelton, IV et al. | |
| 11,504,119 | B2 | 11/2022 | Shelton, IV et al. | |
| 11,504,124 | B2 | 11/2022 | Patel et al. | |
| 11,510,743 | B2 | 11/2022 | Shelton, IV et al. | |
| 11,517,312 | B2 | 12/2022 | Wixey | |
| 11,517,325 | B2 | 12/2022 | Shelton, IV et al. | |
| 11,518,048 | B2 | 12/2022 | Saraliev et al. | |
| 2014/0148816 | A1* | 5/2014 | McDonald ............. | A61B 34/10 606/130 |
| 2014/0362199 | A1 | 12/2014 | Popovic et al. | |
| 2015/0305673 | A1* | 10/2015 | Goldman ............... | A61B 5/743 600/476 |
| 2020/0405399 | A1* | 12/2020 | Steinberg ............... | A61B 90/50 |
| 2021/0315637 | A1 | 10/2021 | Ida et al. | |

* cited by examiner

SYSTEM AND METHOD FOR PORT PLACEMENT IN A SURGICAL ROBOTIC SYSTEM

CROSS-REFERENCE TO RELATED APPLICATIONS

This application claims the benefit of the filing date of provisional U.S. Patent Application No. 63/398,246 filed on Aug. 16, 2022. The entire disclosure of the foregoing application is incorporated by reference herein.

BACKGROUND

Surgical robotic systems are currently being used in minimally invasive medical procedures. Some surgical robotic systems include a user console controlling a surgical robotic arm and a surgical instrument having an end effector (e.g., forceps or grasping instrument) coupled to and actuated by the robotic arm.

Port placement in robotic surgery can be time consuming if the surgeon is expecting to follow established setup guidance.

SUMMARY

According to one embodiment of the present disclosure, a surgical robotic system is disclosed. The surgical robotic system includes a robotic arm including a surgical instrument coupled thereto, a computer configured to calculate port placement locations based on an image of a patient and a type of procedure to be performed, and a printing device. The printing device is configured to print a template of the port placement locations on a transparent substrate for placement on the patient based on the port placement locations calculated by the computer.

In an aspect, the transparent substrate may be a polyester film.

In an aspect, at least a portion of an underside of the transparent substrate may include an adhesive layer for adhering the transparent substrate to the patient.

In an aspect, the printing device may be configured to print the template of port placement locations on the transparent substrate by engraving the port placement locations through the transparent substrate.

In an aspect, the system may further include a transparent substrate configured to be engraved by the printing device wherein the transparent substrate includes at least one preformed cutout extending through a thickness thereof.

In an aspect, the template of port placement locations printed on the transparent substrate may include port placement locations designated for at least one of a right arm, a left arm, a reserve arm, and a camera arm.

In an aspect, the system may further include an imaging device configured to capture an image of the patient.

In an aspect, the system may further include a projector configured to project a projection of the template of port placement locations on the patient.

In an aspect, the projector may be adjustable to resize or move the projection of the template of port placement locations on the patient.

According to another embodiment of the present disclosure, a method for mapping port placement locations is disclosed. The method includes calculating port placement locations based on an image of a patient and a type of procedure to be performed and printing a template of the port placement locations on a transparent substrate for placement on the patient based on the port placement locations calculated by the computer.

In an aspect, the method may further include capturing the image of the patient with an imaging device.

In an aspect, printing the template of the port placement locations on the transparent substrate may include engraving the port placement locations through the transparent substrate.

In an aspect, printing the template of the port placement locations on the transparent substrate may include printing the template of the port placement locations on a polyester film.

In an aspect, printing the template of the port placement locations on the transparent substrate may include printing the template of the port placement locations on a transparent film having an adhesive disposed on an underside thereof.

In an aspect, printing the template of the port placement locations on the transparent substrate may include printing port placement locations designated for at least one of a right arm, a left arm, a reserve arm, and a camera arm.

In an aspect, the method may further include projecting an image of the template of the port placement locations on the patient using a projector.

According to another aspect of the present disclosure, a surgical accessory for aiding in access port placement includes a transparent substrate formed from a polyester film, an adhesive layer an adhesive layer disposed on a tissue contacting surface of the transparent substrate, and at least one marking designating access port insertion disposed on the transparent substrate.

In an aspect, the at least one marking is calculated based on an image of a patient.

In an aspect, the at least one marking is printed on the transparent substrate based on the image.

BRIEF DESCRIPTION OF THE DRAWINGS

Various embodiments of the present disclosure are described herein with reference to the drawings wherein.

DETAILED DESCRIPTION

Figure 1:
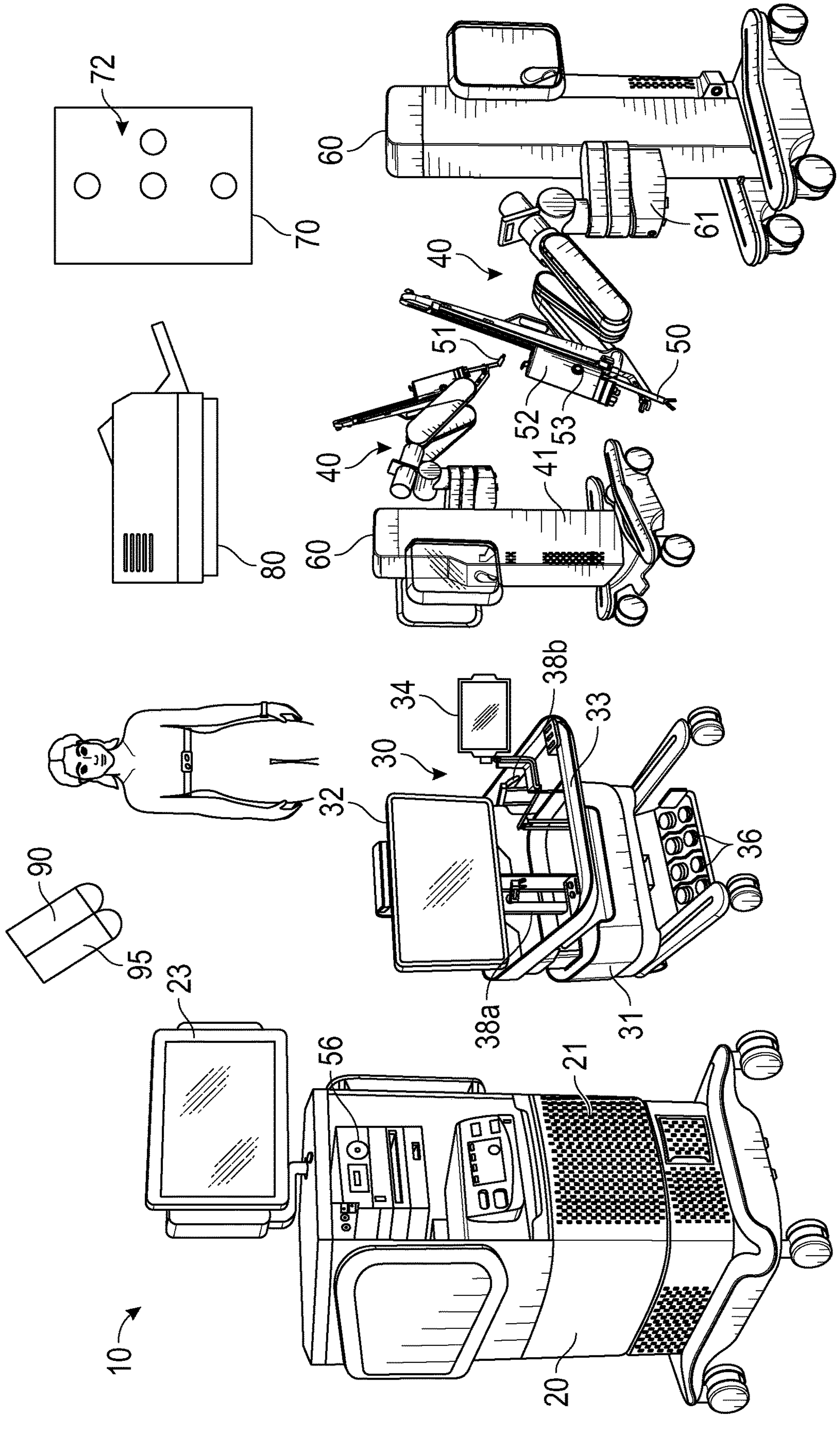
FIG. 1 is a schematic illustration of a surgical robotic system including a control tower, a console, and one or more surgical robotic arms each disposed on a mobile cart according to an embodiment of the present disclosure.

Embodiments of the presently disclosed surgical robotic system are described in detail with reference to the drawings, in which like reference numerals designate identical or corresponding elements in each of the several views. As used herein the term "proximal" refers to the portion of the surgical robotic system and/or the surgical instrument coupled thereto that is closer to a base of a robot, while the term "distal" refers to the portion that is farther from the base of the robot.

As will be described in detail below, the present disclosure is directed to a surgical robotic system, which includes a user console, a control tower, and one or more mobile carts having a surgical robotic arm coupled to a setup arm. The user console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

This disclosure describes a surgical robotic system that includes a printing device for printing a port placement template that may be adhered to the patient and used to map port placement locations on the patient. Port placement in robotic surgery can be time consuming if the surgeon is expecting to follow established setup guidance. In order to allow for more uniform placement, a method of transferring port placement measurements and locations to a transparent sheet, via a combination of laser engraving or laser printing, and then sterilizing is disclosed. The sheet can then be placed over the patient and using anatomical reference points port placement can be marked out through the holes in the transparency.

With reference to FIG. 1, a surgical robotic system 10 includes a control tower 20, which is connected to all of the components of the surgical robotic system 10 including a user console 30, one or more mobile carts 60, and a printing device 80 configured to print a template for port placement locations on a substrate 70. The surgical robotic system 10 may additionally include a camera 90 configured to capture an image of a patient and a projector 95 configured to project an image of the template of port placement locations 72 on the patient. Each of the mobile carts 60 includes a robotic arm 40 having a surgical instrument 50 removably coupled thereto. The robotic arms 40 also couple to the mobile cart 60. The robotic system 10 may include any number of mobile carts 60 and/or robotic arms 40.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In aspect, the surgical instrument 50 may be a surgical port configured to be inserted through the patient's skin to enable insertion of another surgical instrument through the port into the surgical site.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 and output the processed video stream.

The user console 30 includes a first display 32, which displays a video feed of the surgical site provided by camera 51 of the surgical instrument 50 disposed on the robotic arm 40, and a second display 34, which displays a user interface for controlling the surgical robotic system 10. The first and second displays 32 and 34 are touchscreens allowing for displaying various graphical user inputs.

The user console 30 also includes a plurality of user interface devices, such as foot pedals 36 and a pair of handle controllers **38*a* and 38*b* which are used by a user to remotely control robotic arms 40. The user console further includes an armrest 33 used to support clinician's arms while operating the handle controllers 38*a* and 38*b***.

The control tower 20 includes a display 23, which may be a touchscreen, and outputs on the graphical user interfaces (GUIs). The control tower 20 also acts as an interface between the user console 30 and one or more robotic arms 40. In particular, the control tower 20 is configured to control the robotic arms 40, such as to move the robotic arms 40 and the corresponding surgical instrument 50, based on a set of programmable instructions and/or input commands from the user console 30, in such a way that robotic arms 40 and the surgical instrument 50 execute a desired movement sequence in response to input from the foot pedals 36 and the handle controllers **38*a* and 38*b***.

Each of the control tower 20, the user console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
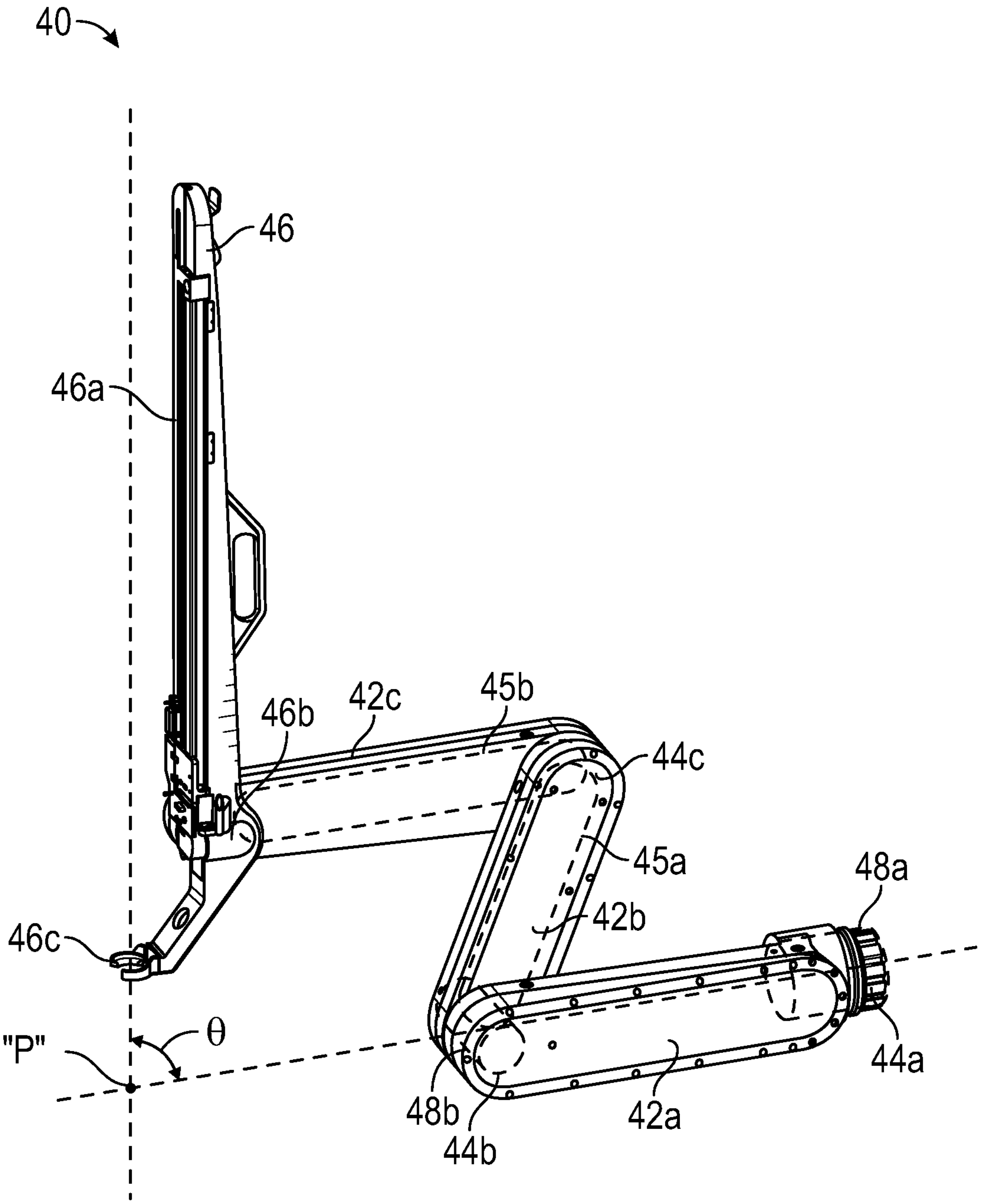
FIG. 2 is a perspective view of a surgical robotic arm of the surgical robotic system of FIG. 1 according to an embodiment of the present disclosure.
Figure 3:
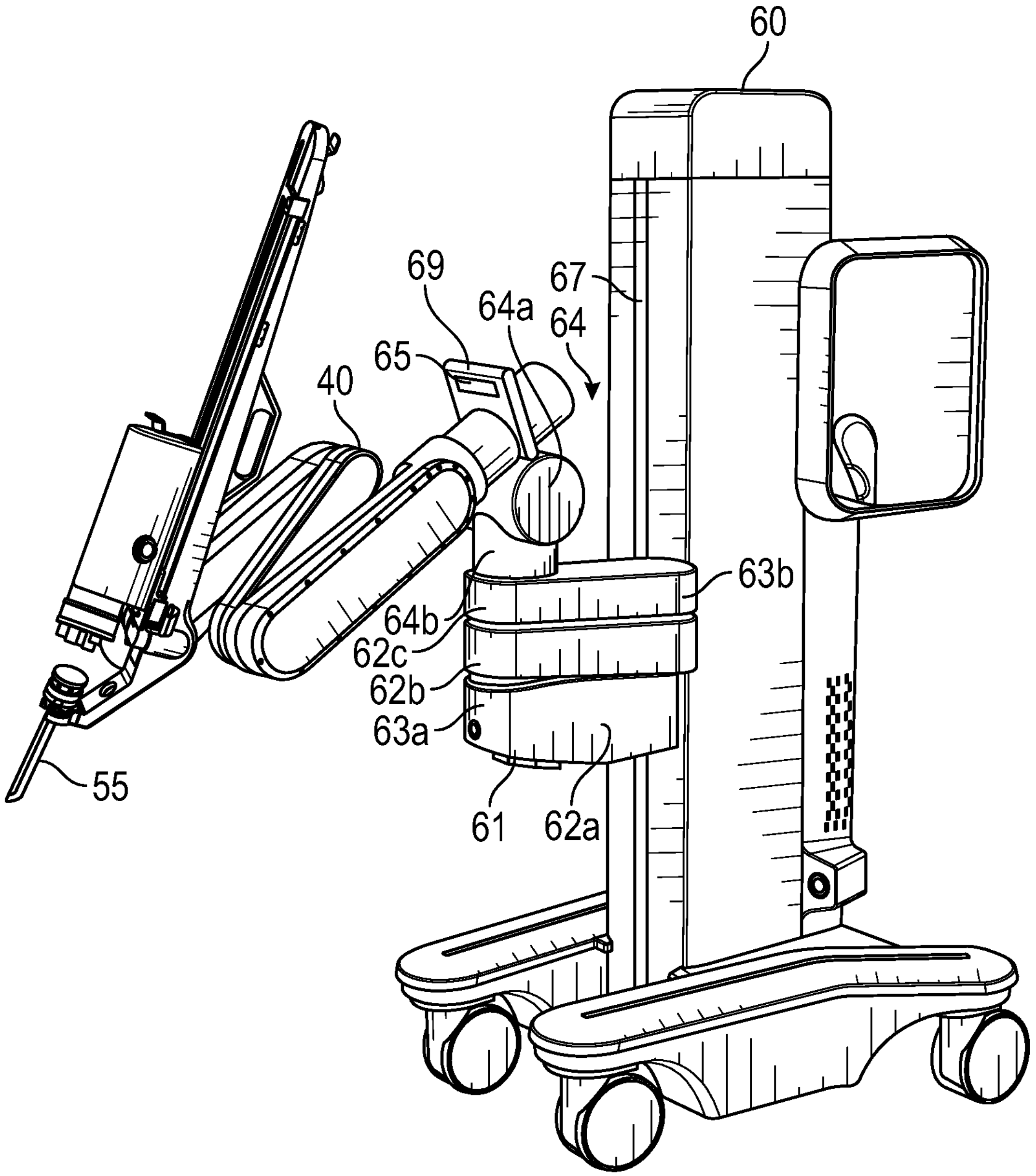
FIG. 3 is a perspective view of a mobile cart having a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. Other configurations of links and joints may be utilized as known by those skilled in the art. The joint 44*a* is configured to secure the robotic arm 40 to the mobile cart 60 and defines a first longitudinal axis. With reference to FIG. 3, the mobile cart 60 includes a lift 67 and a setup arm 61, which provides a base for mounting of the robotic arm 40. The lift 67 allows for vertical movement of the setup arm 61. The mobile cart 60 also includes a display 69 for displaying information pertaining to the robotic arm 40. In embodiments, the robotic arm 40 may include any type and/or number of joints.

The setup arm 61 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62*a*, 62*b*, 62*c* as well as the lift 67. In embodiments, the setup arm 61 may include any type and/or number of joints.

The third link 62*c* may include a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and a holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. In other words, the pivot point "P" is a remote center of motion (RCM) for the robotic arm 40. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic access port 55 (FIG. 3) held by the holder 46. The holder 46 also includes a port latch 46*c* for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
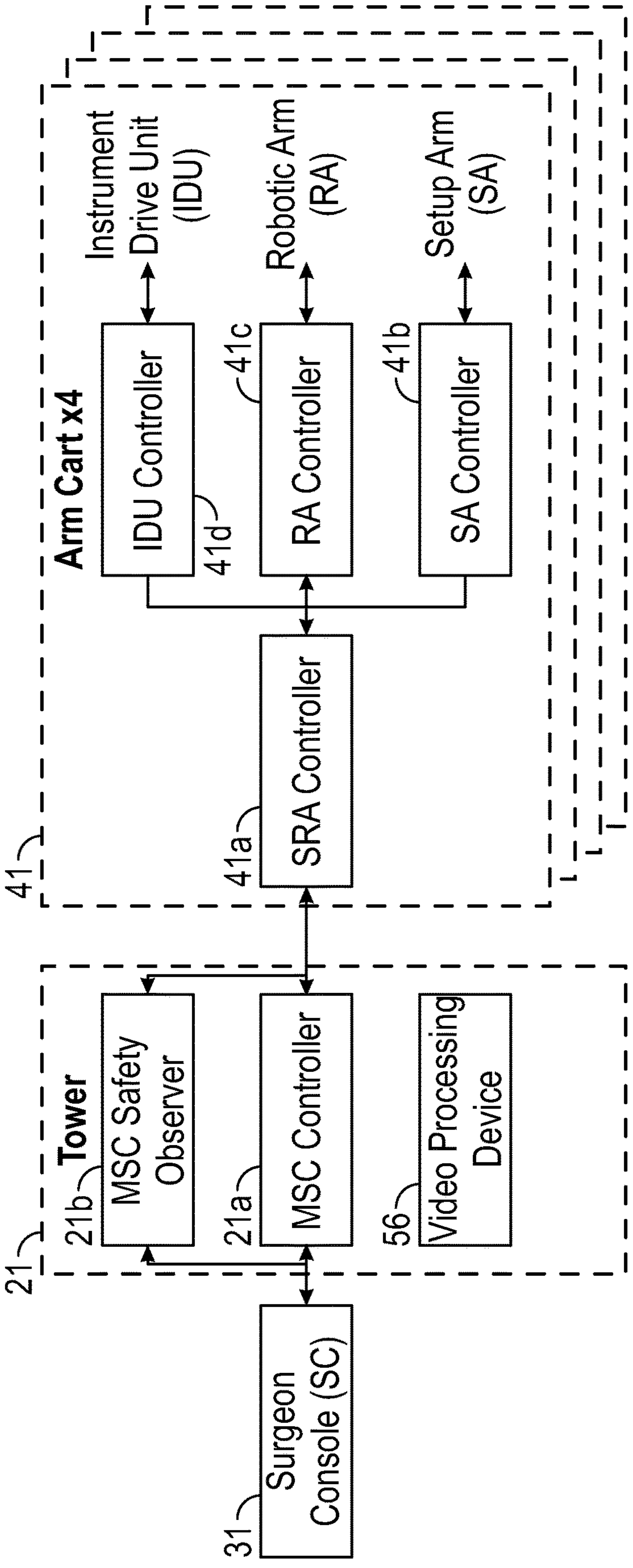
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the user console 30 about the current position and/or orientation of the handle controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the user console 30 to provide haptic feedback through the handle controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the mobile cart 60, the robotic arm 40, and the IDU 52. The main cart controller 41*a* also communicates actual joint angles back to the controller 21*a*.

Each of joints 63*a* and 63*b* and the rotatable base 64 of the setup arm 61 are passive joints (i.e., no actuators are present therein) allowing for manual adjustment thereof by a user. The joints 63*a* and 63*b* and the rotatable base 64 include brakes that are disengaged by the user to configure the setup arm 61. The setup arm controller 41*b* monitors slippage of each of joints 63*a* and 63*b* and the rotatable base 64 of the setup arm 61, when brakes are engaged or may be freely moved by the operator when brakes are disengaged, but do not impact controls of other joints. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the handle controller controlling the robotic arm 40, e.g., the handle controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the handle controllers 38*a* may be embodied as a coordinate position and roll-pitch-yaw (RPY) orientation relative to a coordinate reference frame, which is fixed to the user console 30. The desired pose of the instrument 50 is relative to a fixed frame on the robotic arm 40. The pose of the handle controller 38*a* is then scaled by a scaling function executed by the controller 21*a*. In embodiments, the coordinate position may be scaled down and the orientation may be scaled up by the scaling function. In addition, the controller 21*a* may also execute a clutching function, which disengages the handle controller 38*a* from the robotic arm 40. In particular, the controller 21*a* stops transmitting movement commands from the handle controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the handle controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
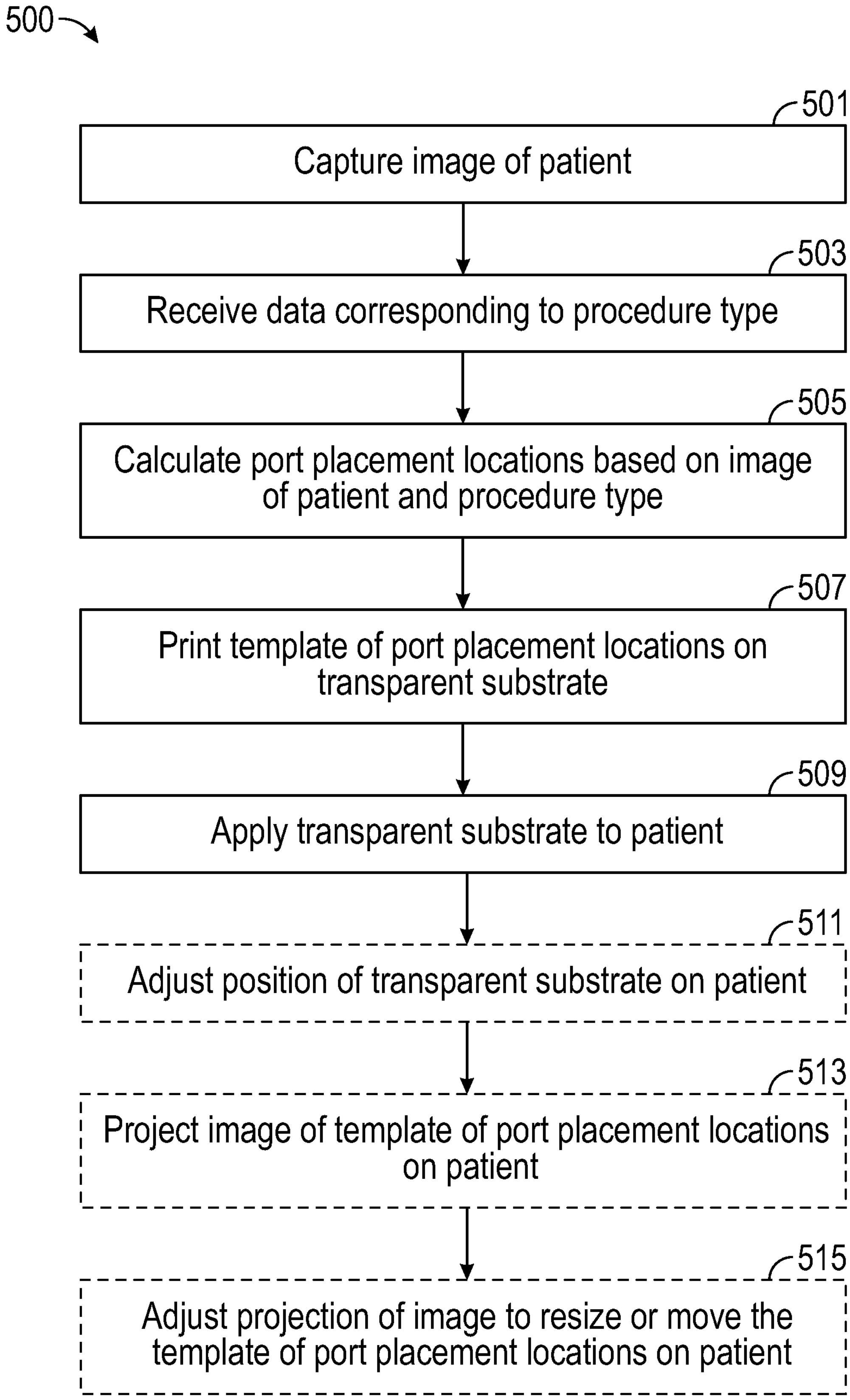
FIG. 5 is a flowchart illustrating a method for mapping port placement locations on a patient according to an aspect of the disclosure.
Figure 6:
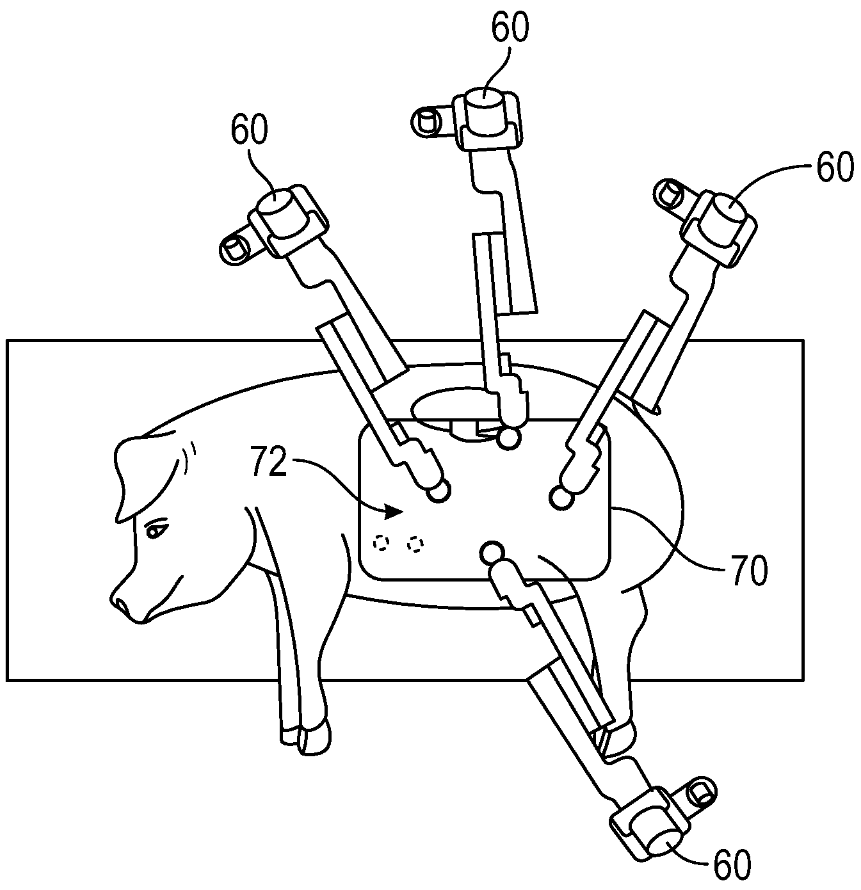
FIG. 6 is a view of a transparent substrate, having a template for port placement locations printed thereon, placed on a patient according to an aspect of the disclosure.
Figure 7:
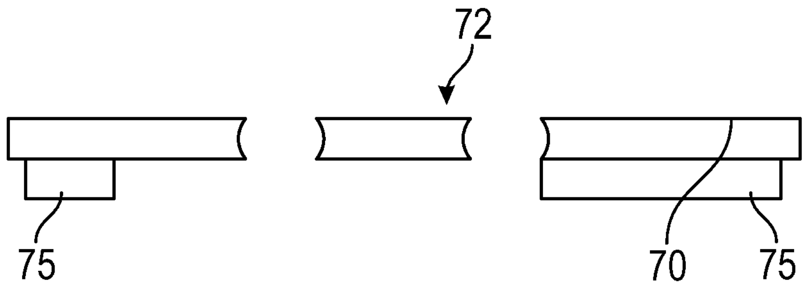
FIG. 7 is a cross-sectional view of a transparent substrate having a template for port placement locations printed thereon according to an aspect of the disclosure.

With continued reference to FIG. 1 and with additional reference to FIGS. 5-7, the present disclosure provides a surgical accessory, i.e., a transparent substrate 70 including port placement locations 72, for aiding in access port placement. The present disclosure also provides an algorithm for making the surgical accessory. The algorithm may be embodied as software instructions executed by a controller, e.g., the controller 21*a* or any other suitable controller, computer, or processor. The algorithm is configured to calculate port placement locations for a particular patient, for example, based on an image of the patient and/or the specific procedure to be performed. Subsequent to calculating the port placement locations, the printing device 80 prints a template of the port placement locations 72 on a transparent substrate 70 for placement on the patient based on the port placement locations calculated by the computer.

In an aspect, the transparent substrate 70 may be a polyester film and may include an adhesive layer 75 on an underside of the transparent substrate 70 for adhering the transparent substrate 70 to the patient. The adhesive layer 75 may cover an entire underside (i.e., patient contacting surface) of the transparent substrate 70 or only one or more portions thereof, e.g., along the perimeter, around placement locations 72, etc. Additionally, the transparent substrate 70 may include dimensional markings. As illustrated best in FIG. 7, the transparent substrate 70 may include at least one preformed cutout extending through a thickness of the transparent substrate 70.

As described above, the printing device 80 is configured to print the template of port placement locations 72 on the transparent substrate 70, for example by engraving the port placement locations 72 through the transparent substrate 70. The template of port placement locations 72 printed on the transparent substrate 70 may include port placement locations designated for the robotic arms 40, e.g., at least one of a right arm, a left arm, a reserve arm, and/or a camera arm, depending on the procedure being performed.

In an aspect, the camera 90 captures an image of the patient and the algorithm utilizes the image captured by the camera 90 to calculate the port placement locations. In addition to printing the template for port placement locations 72 on the transparent substrate 70, the surgical system 10 may also include a projector 95 that projects an image of the port placement locations 72 on the patient. The projector 95 may be adjustable to resize or move the projected image relative to the patient.

FIG. 5 illustrates a method for mapping port placement locations, and is illustrated as method 500. Method 500 may be an algorithm executed by a processor or controller of any component, or combination of components, of surgical robotic system 10. Although method 500 is illustrated and described as including specific steps, and in a specific order, method 500 may be carried out with fewer or more steps than described and/or in any order not specifically described.

Method 500 begins at step 501 where an image of the patient is captured, for example, by a camera 90. In step 503, the system 10 receives data corresponding to the procedure type and/or the patient. Such data may be manually input by a clinician in step 503, for example. In step 505, the system 10 calculates port placement locations based on the image captured in step 501 and the data received in step 503.

In step 507, the printing device 80 prints a template of port placement locations 72 on a transparent substrate 70. Step 507 may include engraving the port placement locations through the transparent substrate 70. Additionally, or alternatively, step 507 may include printing port placement locations designated for the robotic arms 40, e.g., at least one of a right arm, a left arm, a reserve arm, and a camera arm.

In step 509, the transparent substrate 70 is placed on the patient's skin. In an aspect, a user may adhere the transparent substrate 70 to the patient's skin for example, before or after optionally adjusting the position of the transparent substrate 70 to the patient's skin in step 511. Another optional step of method 500 is step 513, where an image of the template of port placement locations 72 is projected onto the patient's skin via the projector 95. Once the image is projected onto the patient's skin, the projector 95 may be adjusted at step 515 so as to resize or move the template of port placement locations 72 relative to the patient's skin.

Figure 8:
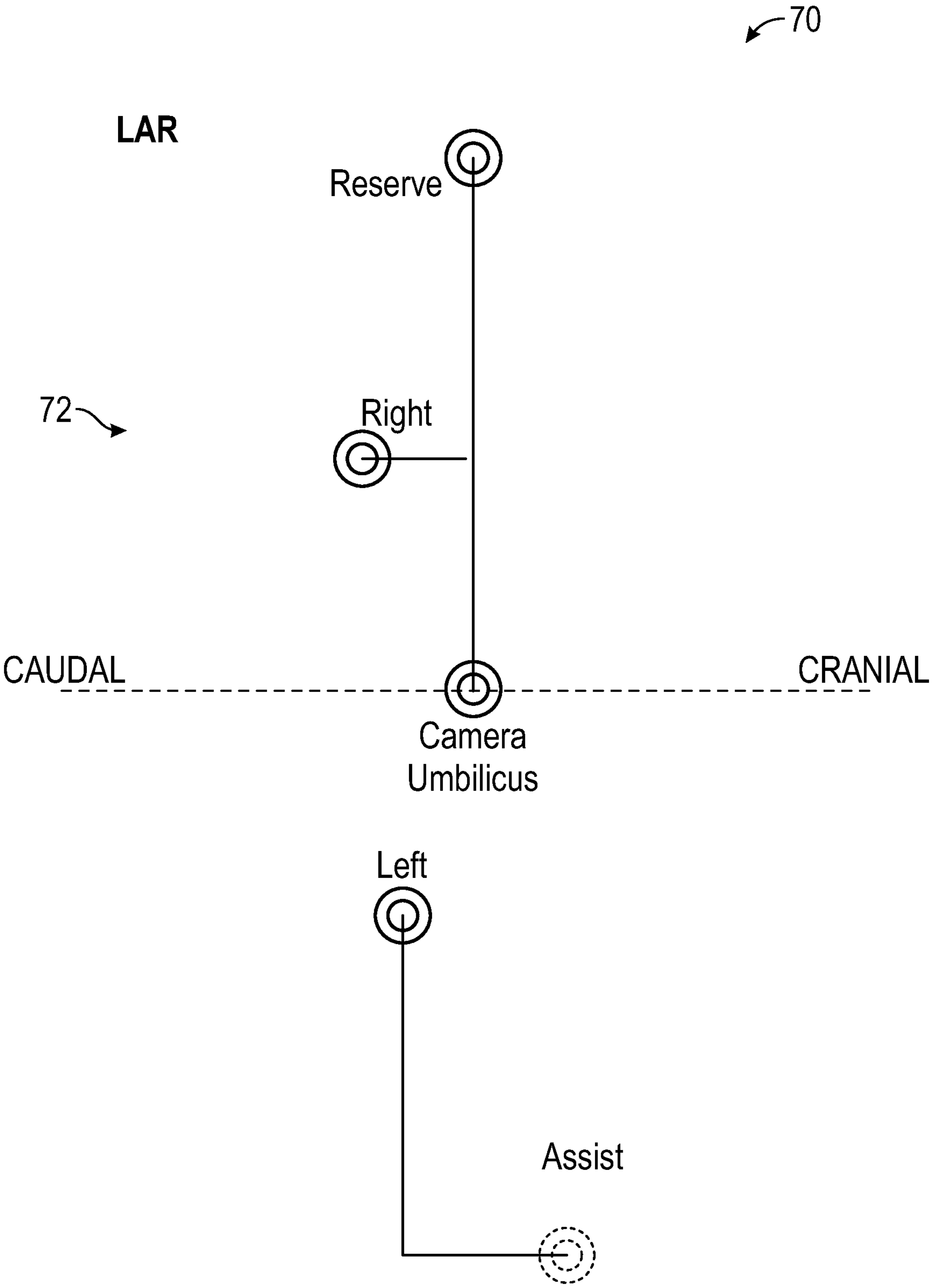
FIG. 8 is an example of a surgical accessory for aiding in access port placement in accordance with an aspect of the disclosure.

FIG. 8 illustrates an example of a surgical accessory (e.g., a transparent substrate 70) including a template of port placement locations 72. The surgical accessory (e.g., transparent substrate includes markings for "reserve", "right", "camera umbilicus", "left", and "assist".

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical robotic system, comprising:

a robotic arm including a surgical instrument coupled thereto;

a computer configured to calculate port placement locations based on an image of a patient and a type of procedure to be performed; and a printing device configured to print, subsequent to the computer calculating the port placement locations, a patient-specific template of the port placement locations on a transparent substrate for placement on the patient, wherein the patient-specific template includes:

an anatomical reference marking for aligning the transparent substrate with an anatomical reference point of the patient; and a plurality of port placement markings corresponding to the calculated port placement locations, and wherein the plurality of port placement markings include port placement designators for respective robotic arms.

2. The surgical robotic system of claim 1, wherein the transparent substrate is a polyester film.

3. The surgical robotic system of claim 1, wherein at least a portion of an underside of the transparent substrate includes an adhesive layer for adhering the transparent substrate to the patient.

4. The surgical robotic system of claim 1, wherein the printing device is configured to print the template of port placement locations on the transparent substrate by engraving the port placement locations through the transparent substrate.

5. The surgical robotic system of claim 1, further comprising a transparent substrate configured to be engraved by the printing device, wherein the transparent substrate includes at least one preformed cutout extending through a thickness thereof.

6. The surgical robotic system of claim 1, wherein the template of port placement markings designated for respective robotic arms include port placement markings designated for at least one of a right arm, a left arm, a reserve arm, and a camera arm.

7. The surgical robotic system of claim 1, further comprising an imaging device configured to capture an image of the patient.

8. The surgical robotic system of claim 1, further comprising a projector configured to project a projection of the template of port placement locations on the patient.

9. The surgical robotic system of claim 8, wherein the projector is adjustable to resize or move the projection of the template of port placement locations on the patient.

10. The surgical robotic system of claim 1, wherein the anatomical reference marking includes a camera marking.

11. A method for mapping port placement locations comprising:

calculating port placement locations based on an image of a patient and a type of procedure to be performed; and printing, subsequent to the calculating, a patient-specific template of the port placement locations on a transparent substrate for placement on the patient based on the port placement locations, wherein the patient-specific template includes:

an anatomical reference marking for aligning the transparent substrate with an anatomical reference point of the patient; and a plurality of port placement markings corresponding to the calculated port placement locations, and wherein the plurality of port placement markings include port placement designators for respective robotic arms.

12. The method of claim 11, further comprising capturing the image of the patient with an imaging device.

13. The method of claim 11, wherein printing the template of the port placement locations on the transparent substrate includes engraving the port placement locations through the transparent substrate.

14. The method of claim 11, wherein printing the template of the port placement locations on the transparent substrate includes printing the template of the port placement locations on a polyester film.

15. The method of claim 11, wherein printing the template of the port placement locations on the transparent substrate includes printing the template of the port placement locations on a transparent film having an adhesive disposed on an underside thereof.

16. The method of claim 11, wherein the template of port placement markings designated for respective robotic arms include port placement markings designated for at least one of a right arm, a left arm, a reserve arm, and a camera arm.

17. The method of claim 11, further comprising projecting an image of the template of the port placement locations on the patient using a projector.

18. The method of claim 17, further comprising adjusting the projector to resize or move the image of the template of the port placement locations.

19. A surgical accessory for aiding in access port placement, the surgical accessory comprising:

a transparent substrate formed from a polyester film;

an adhesive layer disposed on a tissue contacting surface of the transparent substrate; and a patient-specific template printed on the transparent substrate, the patient-specific template including:

an anatomical reference marking for aligning the transparent substrate with an anatomical reference point of a patient; and a plurality of markings designating access port insertion locations, wherein the plurality of markings correspond to port placement locations calculated based on an image of a patient, and wherein the plurality of markings include designators for respective robotic arms.

20. The surgical accessory of claim 19, wherein the anatomical reference marking includes a camera marking.

* * * * *